United States Patent
Edwards et al.

(10) Patent No.: US 9,651,198 B2
(45) Date of Patent: May 16, 2017

(54) MODIFIED FLUOROPOLYMER TUBING FOR ROBUST FLUID STREAM CONTINUITY AND METHOD OF MANUFACTURE

(71) Applicants: Mark Edwards, Armonk, NY (US); Aarti Kriplani, Roseland, NJ (US); Alan R. Toth, Newburgh, NY (US); Ruairi Cunningham, Dublin (IE)

(72) Inventors: Mark Edwards, Armonk, NY (US); Aarti Kriplani, Roseland, NJ (US); Alan R. Toth, Newburgh, NY (US); Ruairi Cunningham, Dublin (IE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 324 days.

(21) Appl. No.: 14/387,204

(22) PCT Filed: Mar. 21, 2013

(86) PCT No.: PCT/US2013/033239
§ 371 (c)(1),
(2) Date: Sep. 22, 2014

(87) PCT Pub. No.: WO2013/142658
PCT Pub. Date: Sep. 26, 2013

(65) Prior Publication Data
US 2015/0047725 A1 Feb. 19, 2015

Related U.S. Application Data

(60) Provisional application No. 61/614,214, filed on Mar. 22, 2012.

(51) Int. Cl.
*F17D 1/08* (2006.01)
*B32B 37/16* (2006.01)
(Continued)

(52) U.S. Cl.
CPC .............. *F17D 1/08* (2013.01); *B01L 3/561* (2013.01); *B32B 37/16* (2013.01);
(Continued)

(58) Field of Classification Search
CPC .. F17D 1/08; Y10T 137/8593; Y10T 428/139; B32B 37/16; B32B 38/0036;
(Continued)

(56) References Cited

U.S. PATENT DOCUMENTS 5,800,858 A 9/1998 Bickford et al.
5,964,251 A 10/1999 Reynolds et al.
(Continued)

FOREIGN PATENT DOCUMENTS

EP 0477543 A2 4/1992

OTHER PUBLICATIONS

PCT International Search Report and Written Opinion dated Jun. 10, 2013 (11 Pages).
(Continued)

*Primary Examiner* — Michael C Miggins

(57) ABSTRACT

The present invention discloses a section of tubing including a fluoropolmer tubular body which has an interior surface defining a fluid passage through the tubular body. At least a first portion of the interior surface has a first hydrophobicity which is less than that of the remainder of the tubular body. At least a first portion of the interior surface can have a molar ratio of fluorine to oxygen of no greater than 30 to 1. Products can include the tubular bodies of the present invention attachable to fluid processing instruments such as immunodiagnostic instruments. The present invention also discloses methods for manufacturing the disclosed tubular bodies.

20 Claims, 11 Drawing Sheets

(51) Int. Cl.
*B32B 38/00* (2006.01)
*B32B 38/10* (2006.01)
*B32B 38/16* (2006.01)
*B01L 3/00* (2006.01)
*F16L 11/04* (2006.01)
*G01N 35/10* (2006.01)
*G01N 35/00* (2006.01)
*A61M 39/08* (2006.01)

(52) U.S. Cl.
CPC .......... *B32B 38/0036* (2013.01); *B32B 38/10* (2013.01); *B32B 38/162* (2013.01); *B32B 38/164* (2013.01); *A61M 39/08* (2013.01); *B01L 2200/12* (2013.01); *B01L 2300/165* (2013.01); *B32B 2386/00* (2013.01); *B32B 2597/00* (2013.01); *F16L 11/04* (2013.01); *G01N 35/10* (2013.01); *G01N 2035/00277* (2013.01); *Y10T 137/8593* (2015.04); *Y10T 428/139* (2015.01)

(58) Field of Classification Search
CPC ..... B32B 38/10; B32B 38/152; B32B 38/164; B32B 2386/00; B32B 2597/00; F16L 11/04; B01L 3/561; B01L 2200/12; B01L 2300/165; G01N 35/10; G01N 2035/00277; A61M 39/08

See application file for complete search history.

(56) References Cited

U.S. PATENT DOCUMENTS

| | | |
|---|---|---|
| 6,024,888 A | 2/2000 | Watanabe et al. |
| 6,337,129 B1 | 1/2002 | Watanabe et al. |
| 2009/0041404 A1 | 2/2009 | Stoddart |
| 2010/0170632 A1 | 7/2010 | Gautriaud et al. |
| 2011/0064613 A1 | 3/2011 | Chen |

OTHER PUBLICATIONS

Partial Supplementary EP Search Report dated Sep. 29, 2015 of corresponding European Patent Application No. 13764415.9, 3 Pages.

| Element | FEP Tubing Good (10777) | FEP Tubing Poor (10778) | FEP Tubing Etched (10779) |
|---|---|---|---|
| Carbon | 42.9 | 42.6 | 43.1 |
| $\sigma$ | 0.2 | 0.2 | 0.2 |
| C-C:C-H | 3.0 | 1.4 | 3.2 |
| C-O | 2.5 | 0.4 | 1.2 |
| C=O | 1.1 | 0.2 | 0.9 |
| O-C=O | 0.6 | 0.4 | 0.8 |
| C-F | 1.4 | 1.4 | 1.7 |
| C-$F_2$ | 31.9 | 36.7 | 33.0 |
| C-$F_3$ | 2.4 | 2.1 | 2.3 |
| Fluorine | 54.0 | 56.4 | 53.6 |
| $\sigma$ | 0.2 | 0.2 | 0.2 |
| F-C | 54.0 | 56.4 | 53.6 |
| Nitrogen | 0.73 | Not detected | 0.04 |
| $\sigma$ | 0.08 | | 0.04 |
| Oxygen | 2.34 | 0.74 | 2.91 |
| $\Sigma$ | 0.08 | 0.08 | 0.08 |
| Calcium | Not detected | Not detected | 0.25 |
| $\Sigma$ | | | 0.05 |
| Silicon | Not detected | 0.25 | Not detected |
| $\Sigma$ | | 0.08 | |
| Chlorine | Not detected | 0.03 | 0.15 |
| $\sigma$ | | 0.03 | 0.04 |
| CERAM File | S17e1101 | S17e1104 | S17e1103 |
| | | | |

Good & Poor = TEFLON FEP TE-9302 Ntubing, Etched = FEP 100 tubing.

The quantification model used assumes that the sample volume probed is homogeneous. The error values ($\sigma$) are calculated from the statistical noise on the data and represent one standard deviation confidence limits; i.e. there is a 68% probability that true composition lies between the calculated composition given in the results tables c±$\sigma$. There is a 95% probability that the true composition lies between c±2$\sigma$. If the $\sigma$ value is comparable to c the element is at or very close to its detection limit for the analysis conditions used. Note that the absolute accuracy of the composition results depend upon a number of factors, but the error values enable the significance of compositional differences between physically similar samples to be assessed.

FIG. 10

|  | FEP Tubing Good | FEP Tubing Poor | FEP Tubing Etched |
|---|---|---|---|
| Amorphous Wt% | 86 | 90 | 88 |
| Crystalline Wt% | 14 | 10 | 12 |

Good & Poor = TEFLON FEP TE-9302 N tubing, Etched = FEP 100 tubing.

FIG. 11

MODIFIED FLUOROPOLYMER TUBING FOR ROBUST FLUID STREAM CONTINUITY AND METHOD OF MANUFACTURE

CROSS REFERENCE TO RELATED APPLICATIONS

This application claims priority to U.S. Provisional Application No. 61/614,214 filed Mar. 22, 2012 and entitled TEFLON SURFACE MODIFICATION FOR ROBUST REAGENT FLUID STREAM CONTINUITY, the whole of which is hereby incorporated by reference within.

STATEMENT REGARDING FEDERALLY SPONSORED RESEARCH OR DEVELOPMENT (Not applicable)

BACKGROUND OF THE INVENTION

The present invention relates to instrumentation for the analysis of fluids, and, more particularly, to the fluoropolymer tubing which is used to convey the fluids to, from and within such instrumentation.

Fluid analysis is critical in a wide variety of fields such as, for example, immunology, microbiology, molecular biology and chemistry. In the medical field, in vitro diagnostic testing, is critical in the diagnosis and treatment of disease and patient management. Medical uses for in vitro diagnostic testing may include diagnosis, screening, therapeutic drug monitoring, collecting epidemiological information, monitoring a course of disease, and antimicrobial susceptibility testing. Reliability is essential because the failure of in vitro diagnostic testing may result in misdiagnosis and incorrect, insufficient, unnecessary, or delayed treatment. The consequences to the patient may be serious or life threatening, depending on various factors including the patient's condition and the clinical significance of the diagnostic test. In vitro diagnostic reagents and systems include those used in hospitals, clinical laboratories, satellite medical facilities, physician's offices, pharmacies, and in the home by consumers.

The availability of sensitive instrumentation for fluid analysis continues to improve. Nonetheless, the accuracy of such instrumentation is dependent upon accurate volume and/or reagent concentration detection which in turn requires the reliable detection of bubbles in the analyte or reagent fluid stream being analyzed. Over time, testing volumes have increased and the machines used for such analysis have gotten faster and more sophisticated. The increased speed of the machines means that fluids are being moved faster and faster. This in turn affects fluid dynamics and the fluids being analyzed are increasingly susceptible to breaking up at the higher speeds. This fluid break up affects accurate volume and/or reagent concentration confirmation.

In addition, fluid analysis testing has become increasingly sophisticated. In the medical field, for example, it is not uncommon to perform over 90 tests on a blood sample and to require the use of 2-4 reagents in such tests. Each test may require up to 2-4 fluid additions. One probe of a fluid analysis machine may be exposed to over 240 different fluid compositions related to a given blood sample. It is imperative that the different fluid streams being analyzed do not affect each other where a large range of fluid compositions are being analyzed. The increased speed and test volumes involved with fluid analysis have led to increased volume and reagent concentration check errors and volume check errors can require over 50% of fluid analysis tests to be repeated. Repeat analyses require greater analysis time, less efficiency and increased cost. The greater analysis time may be particularly critical in medical situations where treatment decisions are based on the results of in vitro diagnostic testing.

Thus there is a need to minimize the errors involved in the confirmation of fluid volumes and reagent concentrations in analytic instrumentation.

BRIEF SUMMARY OF THE INVENTION

Fluoropolymer tubing is generally used to convey fluids for fluid analysis. In the present invention, modified fluoropolymer tubing for robust fluid continuity and a method for making such tubing are disclosed. A section of such tubing includes a fluoropolmer tubular body which has an interior surface defining a fluid passage through the tubular body. At least a first portion of the interior surface has a first hydrophobicity which is less than that of the remainder of the tubular body. In an alternative embodiment, the invention discloses a section of such tubing including a fluoropolmer tubular body which has an interior surface defining a fluid passage through the tubular body where at least a first portion of the interior surface has a molar ratio of fluorine to oxygen of no greater than 30 to 1.

The fluoropolymers suitable for the above disclosed tubular bodies include, for example, polytetrafluoroethylene, fluorinated ethylene propylene, and perfluoroalkoxy. Products of the invention include a fluid processing instrument which may be operated to receive fluid and the disclosed fluoropolymer tubular bodies attachable to the fluid processing instrument to deliver fluid to the instrument. The fluid processing instruments can include, for example, immunodiagnostic instruments.

The invention discloses a method for providing a section of tubing comprising a tubular body comprising a fluoropolymer, the tubular body including an interior surface defining a fluid passage through the tubular body. The interior surface of the tubular body has a first hydrophobicity. The method further discloses exposing at least a first portion of the interior surface of the tubular body to an etching agent specific to fluoropolymers after which the first portion has a second hydrophobicity which is less than the first hydrophobicity. In one embodiment, a first molar ratio of fluorine to oxygen of the first portion of the interior surface can be decreased to no greater than 30 to 1. The etching agent specific to fluoropolymers includes an active ingredient such as, for example, sodium naphthalide.

In embodiments, the invention further discloses, prior to exposing the tubular body to the etching agent, heating the etching agent in a separate vessel to a temperature of, for example, between 50° C. and 60° C. During heating, the etching agent can be agitated.

Once the exposure to the etching agent is completed, the etching agent can be withdrawn from the tubular body. In one embodiment, the tubular body then can be treated by flushing the interior surface of the tubular body at least a first time with an alcohol; rinsing the interior surface of the tubular body at least a first time with water; and drying the interior surface of the tubular body.

In other embodiments, following the drying of the tubular body, the tubular body can be annealed to stabilize the chemical chains of the fluoropolymers of the tubular body. Following annealing, the tubular body can be cooled to, for example, room temperature. The tubular body can then be further treated by flushing the interior surface of the tubular body at least a first time with a bleach solution; rinsing the interior surface of the tubular body at least a first time with water; and drying the interior surface of the tubular body.

In yet further embodiments, the invention discloses providing a fluid processing instrument operative to receive a fluid for analysis. The tubular body can be attached to the fluid processing instrument. Fluid can then be conveyed through the fluid passage of the tubular body to the fluid processing instrument for analysis. The fluid processing instrument can include an immunodiagnostic instrument.

BRIEF DESCRIPTION OF THE SEVERAL VIEWS OF THE DRAWINGS

The foregoing summary, as well as the following description of the invention, is better understood when read in conjunction with the appended drawings. For the purpose of illustrating the invention, exemplary constructions are shown in the drawings. The invention is not limited, however, to the specific methods and instrumentalities disclosed herein.

FIG. 10 summarizes the data including surface compositions in atomic percent (At. %) based on the X-ray Photoelectron Spectroscopy discussed in Example 1.

FIG. 11 summarizes the data based on X-ray Diffraction discussed in Example 1.

DETAILED DESCRIPTION OF THE INVENTION

Figure 1:
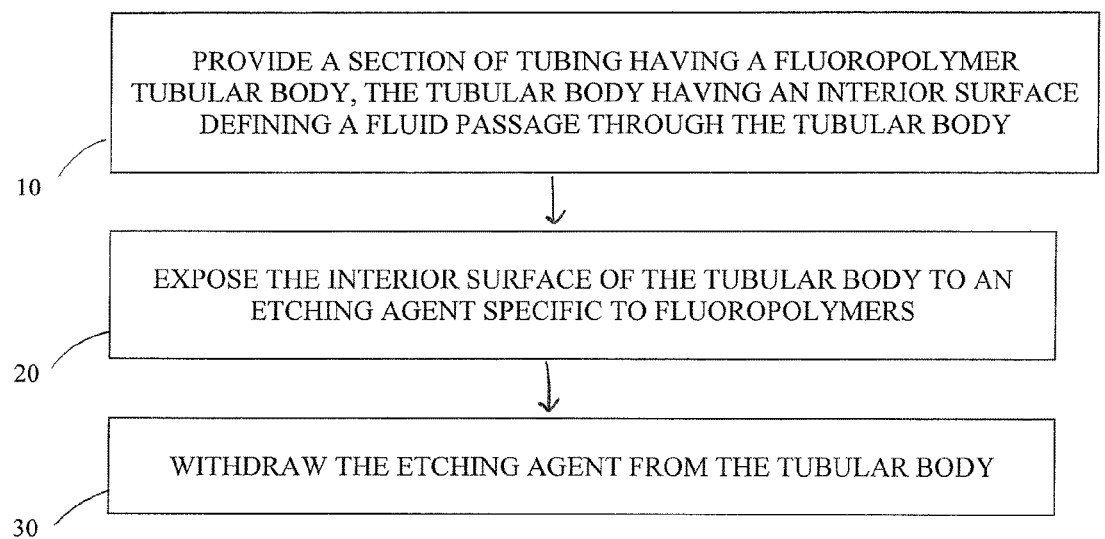
FIG. 1 exemplarily illustrates the method of the present invention including steps of providing a section of tubing, exposing at least a first portion of the interior surface of the tubing's tubular body to an etching agent, and withdrawing the etching agent from the tubular body.

This application claims priority to U.S. Provisional Application No. 61/614,214 filed Mar. 22, 2012 and entitled TEFLON SURFACE MODIFICATION FOR ROBUST REAGENT FLUID STREAM CONTINUITY, the whole of which is hereby incorporated by reference within.

Most fluid analytic machines today employ fluoropolymer tubing for the conveyance of fluids. The present invention discloses a method for addressing the problems related to volume and reagent concentration check errors by disclosing a method for modifying fluoropolymer tubing such as, for example, extruded tubing, to decrease the hydrophobicity of the tubing. The decrease in hydrophobicity results in less fluidic breakup. Accordingly, it is easier to detect bubbles in the fluid stream and to enable more accurate volume and/or reagent concentration confirmation. The fluoropolymer of the tubing of the present invention may include, for example, polytetrafluoroethylene, fluorinated ethylene propylene, and perfluoroalkoxy.

It was recognized in the present invention that the hydrophobicity of fluoropolymer tubing is related to the molar ratio of fluorine to oxygen ratio in the tubing. Typical fluoropolymer tubing has a molar ratio of fluorine to oxygen of at least 60. Fluropolymer tubing consists of a tubular body having an interior surface defining a fluid passage through the tubular body. The interior surface has a first hydrophobicity. The present invention discloses exposing at least a first portion of the interior surface of the tubular body to an etching agent specific to fluoropolmers. The active ingredient of the etching agent cleaves the fluorine atoms from the carbon backbone of the fluoropolymer. The fluorine atoms are replaced with oxygenated functionalities such as hydroxyl, carbonyl, and carboxyl groups. After exposure to the etching agent, the hydrophobicity of the first portion of the interior surface of the tubular body, that is, the second hydrophobicity, is decreased relative to the first hydrophobicity prior to exposure to the etching agent.

The present invention discloses reducing the molar ratio of fluorine to oxygen of the first portion of the interior surface of the tubular body to less than 60 to 1, more preferably to less than 40 to one, and most preferably to less than 30 to one. The roughness of the first portion of the interior surface of the tubular body is reduced by, for example, at least 10 Sa (nm), and more preferably by more than 20 Sa (nm) and even more preferably by more than 35 Sa (nm). In the present invention, surface roughness can be evaluated using methods known to those of ordinary skill in the art, such as, for example, optical profilometry. A white light interferometer is an example of one type of instrument which may be used for such optical profilometry.

The etching agent specific to flouropolymers has an active ingredient which can include sodium naphthalide. Other types of etching agents which can be used in the present invention include sodium etching solutions for rendering fluorocarbons receptive to modern adhesion bonding. In the present invention, at least the first portion of the tubular body where the liquids of interest will be present in the tube is exposed to the etching agent.

Figure 2:
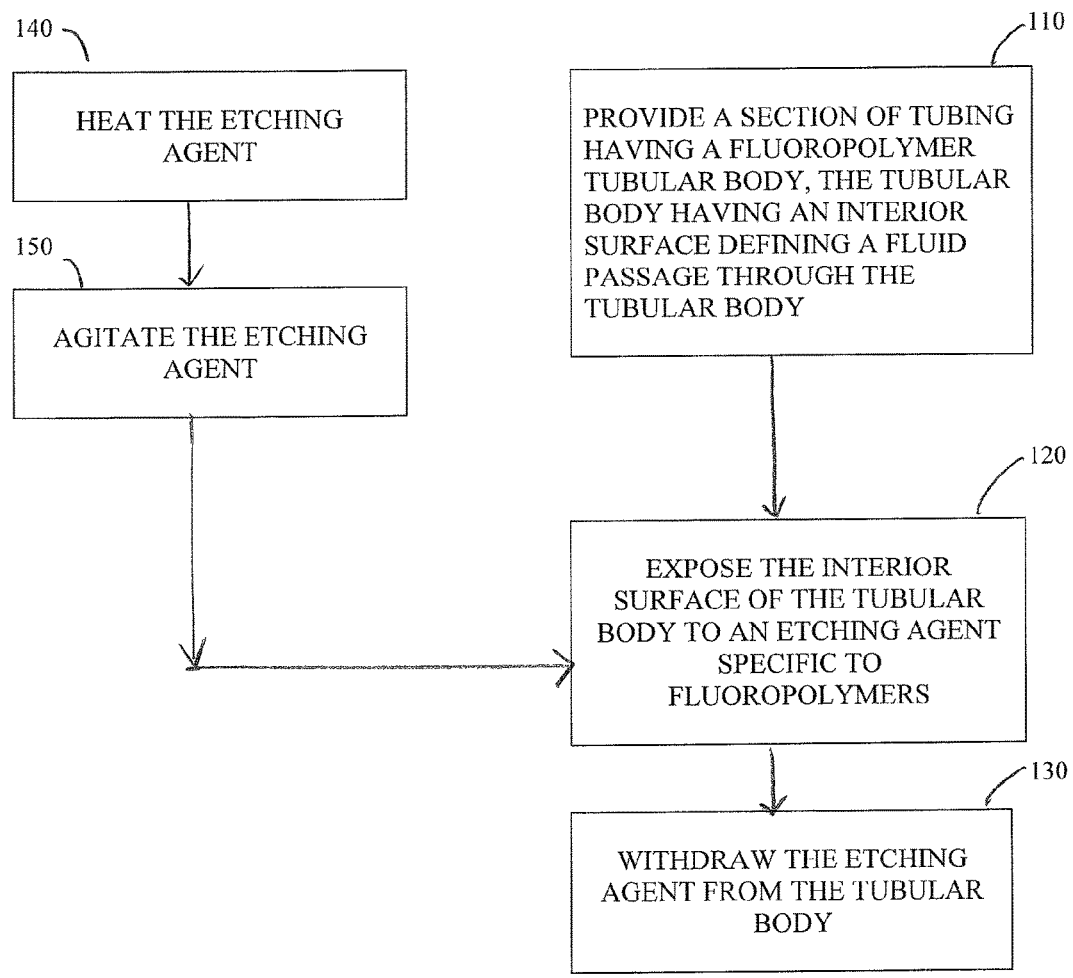
FIG. 2 exemplarily illustrates the method of the present invention including the steps of heating and agitating the etching agent prior to exposing at least a first portion of the interior of the tubular body to the etching agent.

Exemplary steps of method of the present invention are shown in FIG. 1 and FIG. 2. In steps 10 and 110 of FIG. 1 and FIG. 2, respectively, a section of tubing, such as, for example, a section of extruded tubing, is provided having a fluoropolymer tubular body including an interior surface defining a fluid passage through the tubular body. The interior surface of the tubular body has a first hydrophobicity. At least a first portion of the interior surface of the tubular body is exposed to an etching agent specific to fluoropolymers after which the first portion has a second hydrophobicity which is less than the first hydrophobicity, as shown in steps 20 and 120 of FIG. 1 and FIG. 2, respectively.

The molar ratio of fluorine to oxygen on the first portion of the interior surface can be decreased by exposure to the etching agent to no greater than 30 to 1. The exposure time is a function of the crystallinity of the tubing where the greater the tubing crystallinity, the greater the etching time required. The interior surface is preferably exposed for at least one second, and more preferably for at least 30 seconds and even more preferably for 60 seconds. The chemical reaction of the etching agent may be observed visually in a clear tubular body. The reduction in the molar ratio of fluorine to oxygen by the cleaving of fluorine atoms with oxygenated groups results in a carbonaceous layer which renders the clear tubing opaque. After exposing the inner surface of the tubular body to the etching agent, the etching agent may be withdrawn from the tubular body, as shown in steps 30 and 130 of FIG. 1 and FIG. 2, respectively.

Prior to the exposing step, the etching agent can be heated in a separate vessel, as shown in step 140 of FIG. 2, to ensure that the active ingredient of the etching agent is in solution. The etching agent can be heated to a temperature of up to 70° C., and more preferably to a temperature of between 50° C. and 60° C., depending on the recommendations provided by the manufacturer of the etching agent. The method of the present invention can also include agitating the etching agent in the separate vessel while it is being heated, as shown in step 150 of FIG. 2, again to ensure that the active ingredient of the etching agent is in solution. The heating and agitating of the etching agent in order to ensure that the solubility of the etching agent's active ingredient is conducted according to methods known to those of ordinary skill in the art. It is preferable that heating is conducted slowly, for example, for at least 60 minutes, and simultaneously agitated.

Figure 3:
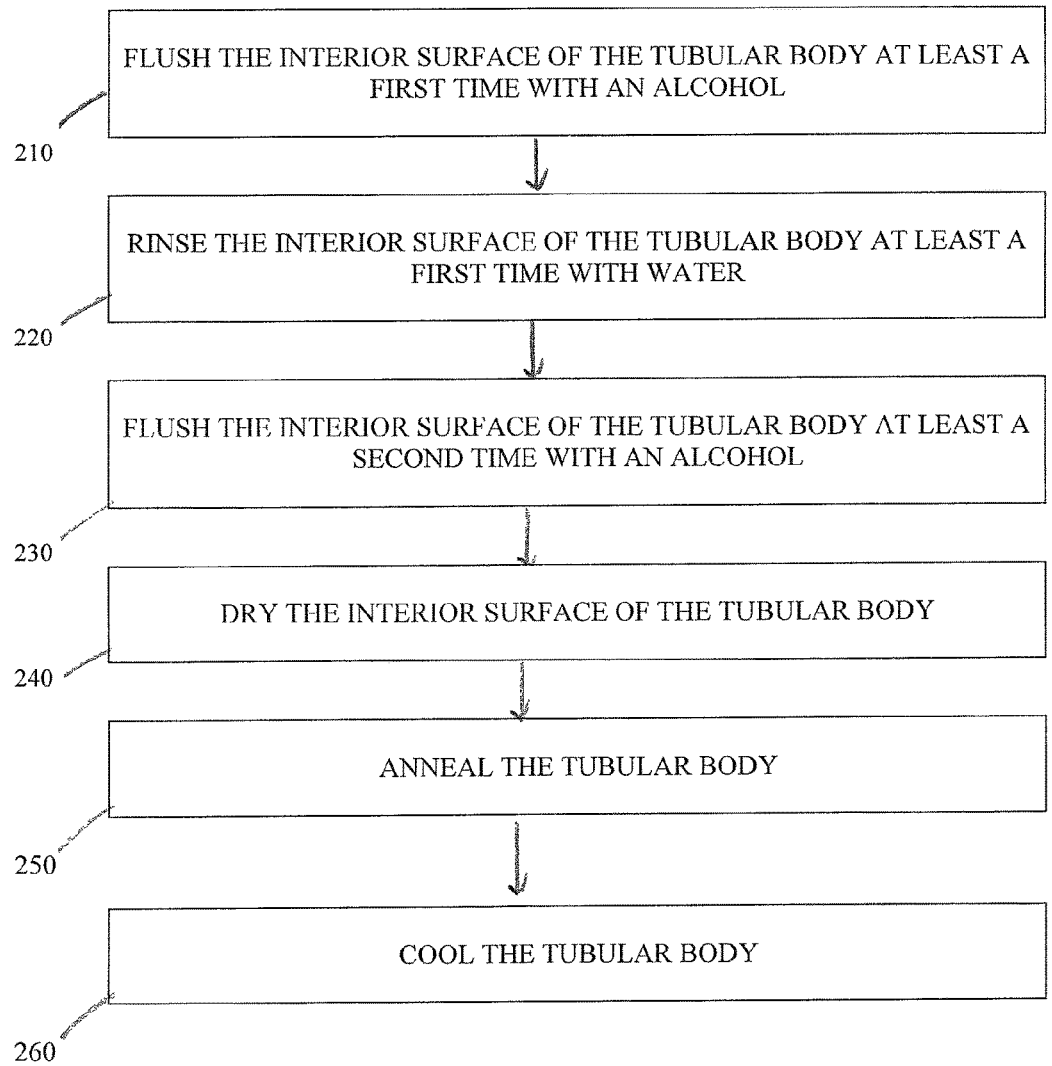
FIG. 3 exemplarily illustrates the method of the present invention including steps of flushing, rinsing, drying, annealing and cooling the tubular body following withdrawal of the etching agent from the tubular body.

The method of the invention further teaches treating the tubular body after the exposure to the etching agent, as shown in FIG. 3. Once the etching agent is withdrawn from the tubular body, as shown in steps 30 and 130 of FIG. 1 and FIG. 2, respectively, the interior surface of the tubular body is flushed at least a first time with an alcohol, such as for example methanol, as shown in step 210 of FIG. 3. The alcohol is used to deactivate the active ingredient of any etching agent remaining in the tubular body. The quantity of alcohol used depends upon the volume of the tubular body exposed to the etching agent. Preferably, 5 to 15 ml of alcohol is used, and more preferably 5 ml of alcohol is used.

The interior surface of the tubular body is then rinsed at least a first time with water, and preferably deionized water, as shown in step 220 of FIG. 3. The quantity of rinsing water used depends upon the volume of the tubular body exposed to the etching agent. Preferably, 5 to 20 ml of water is used, and more preferably 15 ml of water is used. The tubular body can then be flushed at least a second time with an alcohol, such as methanol, as shown in step 230 of FIG. 3, and then dried, as shown in step 240 of FIG. 3. Drying may be accomplished by, for example, using compressed air. Alternatively, drying may be accomplished by using heating device such as an oven.

The tubular body may then be annealed, as shown in step 250 of FIG. 3. Annealing stabilizes the interior surface of the tubular body allowing the changing molecular chains to reorganize to more stable positions. Preferably the full tubular body is placed in a heating device, such as an oven, and heated to a temperature of between 50° C. and 200° C., and more preferably to between 50° C. and 150° C., and most preferably to 100° C. for preferably at least two hours to one week, and more preferably for at least four hours to one week. The tubular body is then cooled, preferably to room temperature, as shown in step 260 of FIG. 3.

Figure 4:
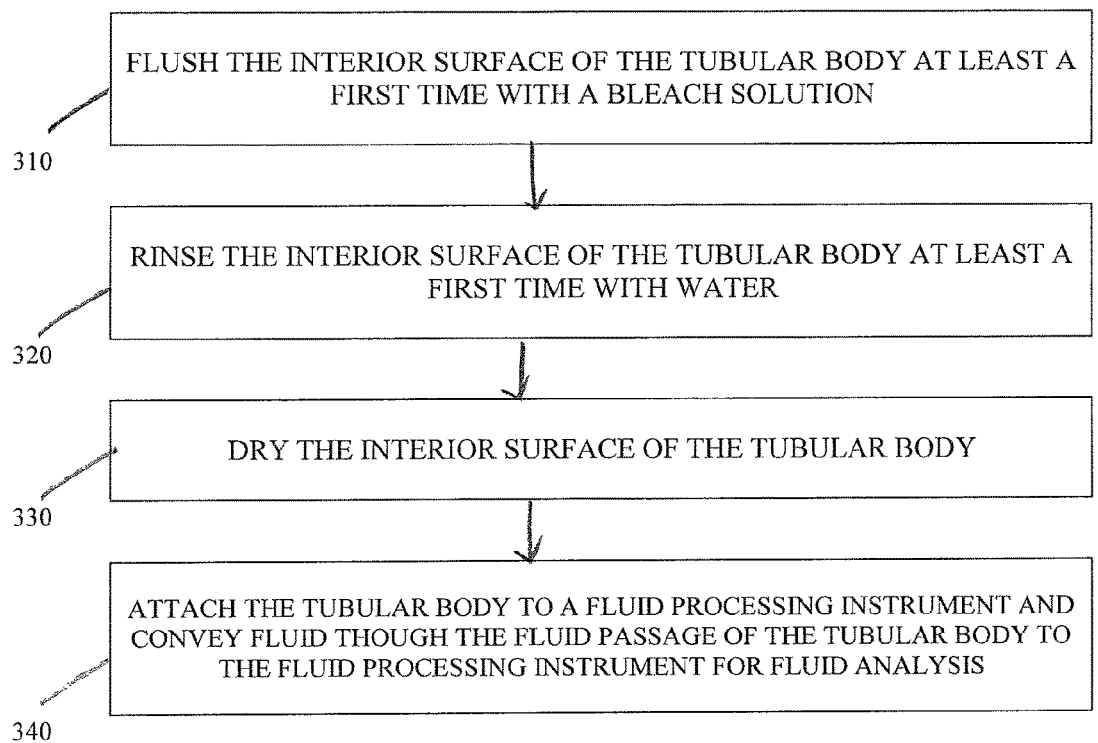
FIG. 4 exemplarily illustrates the method of the present invention including steps of further flushing, rinsing and drying the tubular body following the annealing and subsequent cooling of the tubular body.

FIG. 4 shows post-annealing treatment steps which may be undertaken in accordance with the present invention. In step 310, the interior surface is flushed at least one time with a bleach solution, such as, for example, calcium hypochlorate. The amount of flushing required is again dependent on the tubular volume which has been exposed to the etching agent. The bleach flushing helps to stabilize the hydrophobicity in the tubular body so that the hydrophobicity of the tubular body does not increase with further fluid processing. The flow rate of the bleach can range for 1 ml/min to 10 ml/min and more preferably ranges from 3 ml/min to 6 ml/min and most preferably is 4.5 ml/min.

The interior surface is then rinsed at least one time with water, and preferably deionized water, to remove any remaining bleach solution, as shown in step 320. Finally, the interior surface of the tubular body is dried, as shown in step 330, by, for example, blowing compressed air to remove any residual liquid remaining on the interior surface of the tubular body. Alternatively, a heating device, such as an oven, can be used for drying. The method of the invention further discloses attaching tubular body to a fluid processing instrument, as shown in step 350, and conveying the fluid thorough the fluid passage of the tubular body to the fluid processing instrument for fluid analysis. This fluid processing instrument can include, for example, an immunodiagnostic instrument.

Figure 5:
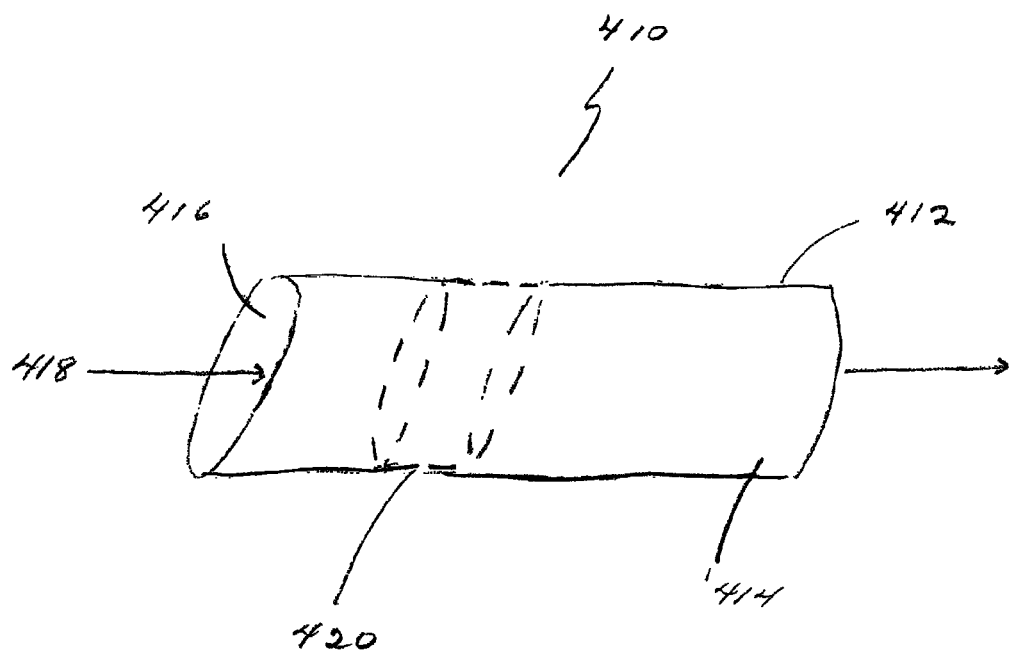
FIG. 5 exemplarily illustrates an article of the present invention where at least a first portion of the interior surface of the tubular body has a reduced fluorine to oxygen molar ratio.
Figure 6:
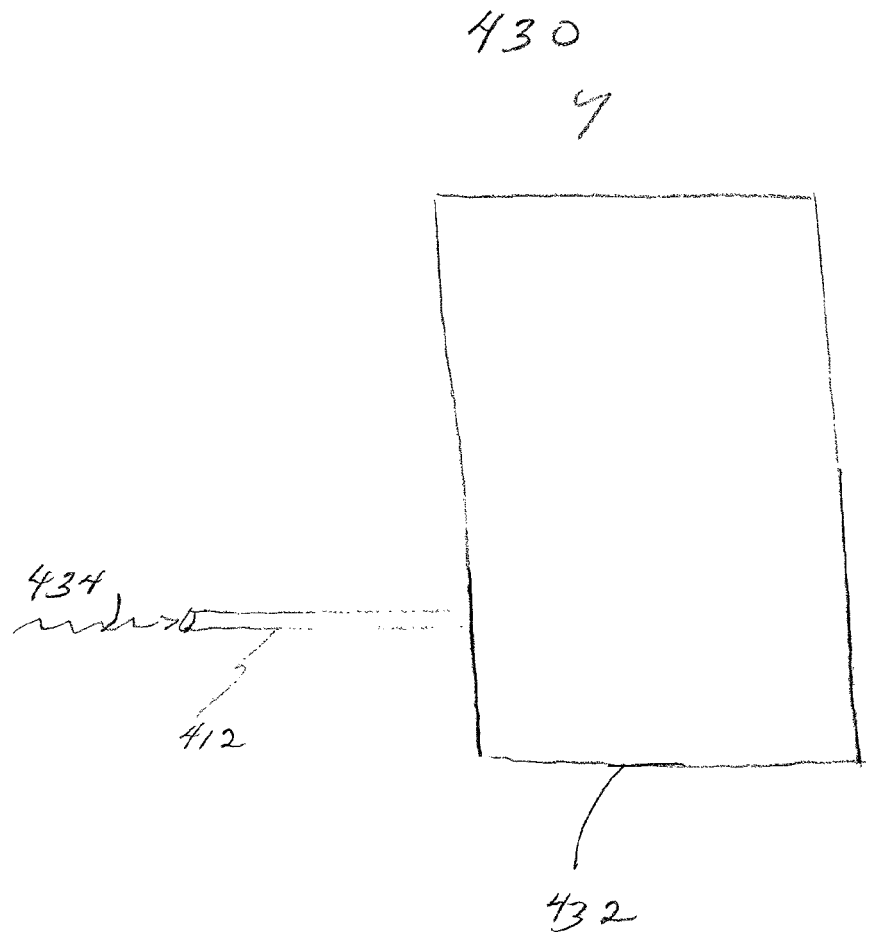
FIG. 6 exemplarily illustrates a product of the present invention including the tubular body of FIG. 5 attachable to a fluid processing instrument.

The present invention also teaches an article which is shown in FIG. 5. The invention discloses a section of tubing 420, such as, for example, an extruded tubing having a tubular body 412 consisting of a fluoropolymer 414. This fluoroploymer may consist of, for example, polytetrafluoroethylene, a fluorinated ethylene propylene, and a perfluoroalkoxy. The tubular body 412 has an interior surface 416 defining a fluid passage 418 through the tubular body 412. At least a first portion 420 of the interior surface 416 has a molar ratio of fluorine to oxygen of no greater than 30 to 1. The invention further teaches a product 430 which includes the tubular body 412 discussed above which can be attached to a fluid processing instrument 432, as shown in FIG. 6. The tubular body enables fluid delivery to the fluid processing instrument 432. The fluid processing instrument can include, for example, a immunodiagnostic instrument.

Figure 7:
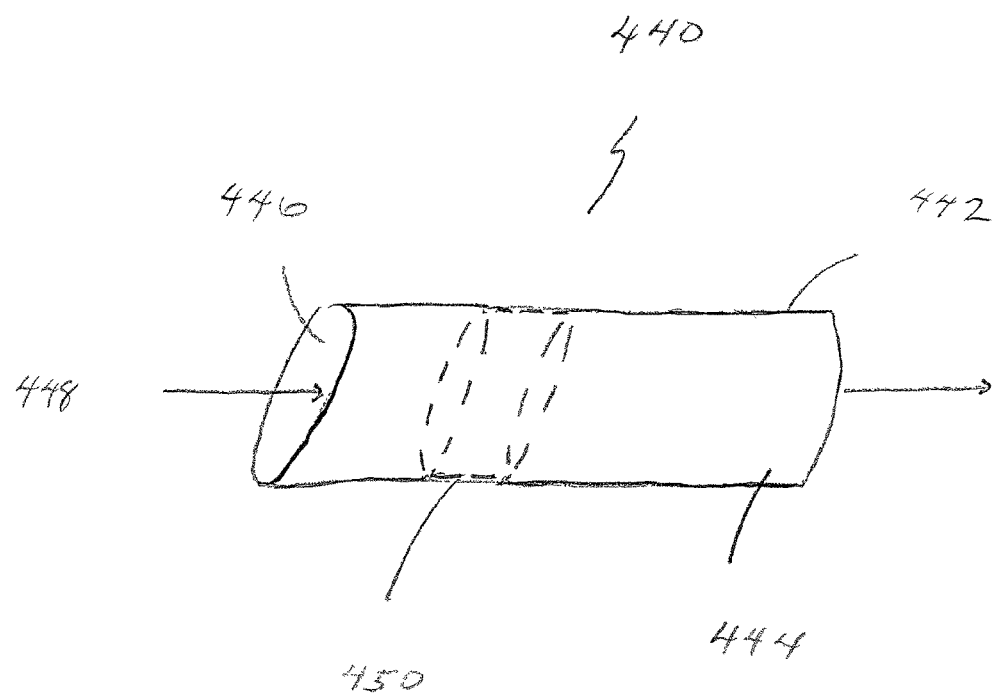
FIG. 7 exemplarily illustrates an article of the present invention where at least the hydrophobicity of a first portion of the interior surface of the tubular body is less than the hydrophobicity of the remainder of the tubular body.
Figure 8:
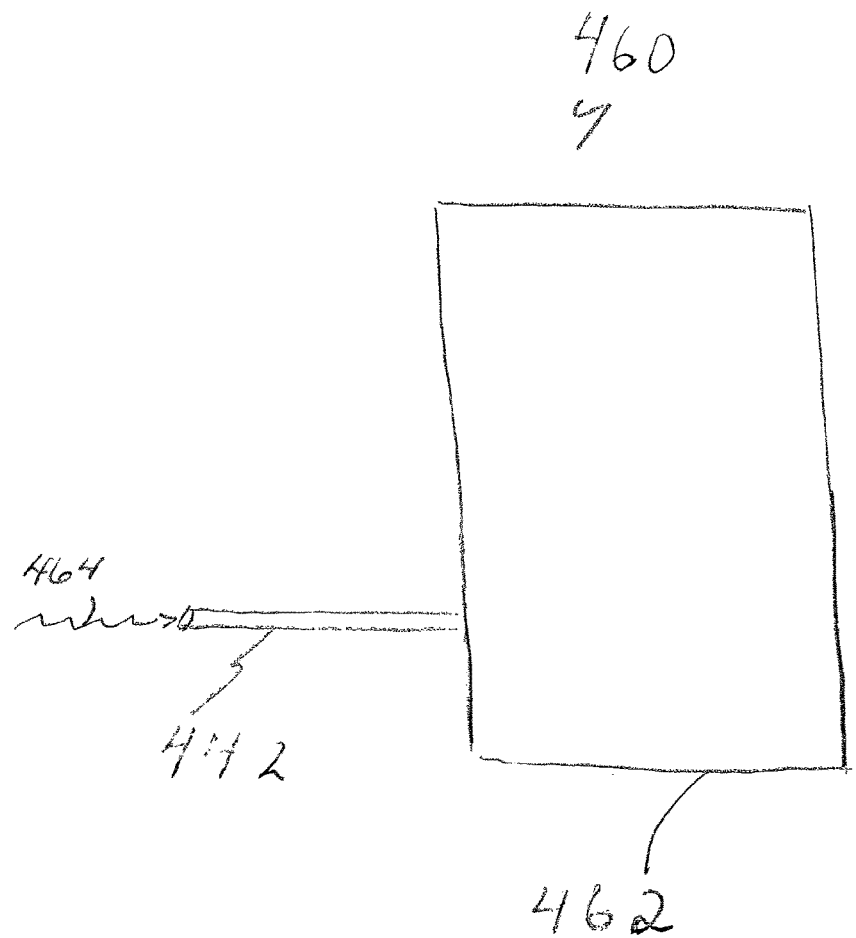
FIG. 8 exemplarily illustrates a product of the present invention including the tubular body of FIG. 7 attachable to a fluid processing instrument.

In addition, the invention teaches an article which includes a section of tubing 440, such as extruded tubing, having a tubular body 442 consisting of a fluoropolymer 444, as shown in FIG. 7. The fluoropolymer may include polytetrafluoroethylene, fluorinated ethylene propylene, or perfluoroalkoxy. The tubular body 442 includes an interior surface 446 defining a fluid passage 338 through the tubular body 442. At least a first portion 450 of the tubular body has a first hydrophobicity less than that of a remainder of the tubular body. The portion 450 of the tubular body 442 has a fluorine to oxygen ratio molar ratio of no greater than 30 to 1, while the remainder of the tubular body has a fluorine to oxygen molar ratio of at least 60 to 1.

The invention also discloses a product 460 including the tubing 442 discussed above which can be attached to a fluid processing instrument 462, as shown in FIG. 6. The tubular body enables the delivery of a fluid 434 to the fluid processing instrument 462. The fluid processing instrument can include, for example, a immunodiagnostic instrument.

The example below illustrates the method and article of the present invention.

Example 1

Testing was conducted to investigate the variation in the hydrophobicity of Fluorinated Ethylene Propylene (FEP)

tubing (outside diameter or OD=2.53 MM, inside diameter or ID=1.5 mm). It had been observed that new batches of the FEP tubing were not performing well and appeared more hydrophobic than the old.

Old (good) and new (poor) samples of FEP tubing consisting of Teflon FEP TE-9302 N material were compared with an etched sample of FEP tubing consisting of FEP 100 material. All the tubing had outside diameter (OD) of 2.53 mm and an inside diameter (ID) of 1.5 mm. Etching was carried out using FluoroEtch. The Fluoroetch was heated to 50° C. and agitated for one minute, and the etchant was then delivered into the interior fluid passage of the tubing. The etchant stripped the fluorine from the FEP carbon backbone at the surface of the FEP material. The fluorine atoms were replaced by hydroxyl/carbonyl/carboxyl groups. The etchant was then withdrawn from the tubing and the tubing was flushed with methanol, rinsed with deionized water, dried and annealed for 1 week at 100° C. After this, the tubing was flushed with bleach, rinsed with deionized water and then dried with compressed air.

The ID surface of each of the good, poor and etched FEP tubing samples surface was chemically analyzed using a combination of X-ray Photoelectron Spectroscopy (XPS) and Time-of-Flight Secondary Ion Mass Spectrometry (ToF-SIMS). X-ray Diffraction (XRD) was then used to investigate any differences in crystallinity.

In the XPS Anaylsis, an approximate 6 mm piece was cut from each of the three good, poor, and etched FEP tubing samples. Each 6 mm piece was then longitudinally sectioned under an optical microscope using a fresh solvent-cleaned uncoated stainless steel razor blade to expose the ID surface for analysis.

XPS measurements were performed with a Kratos Axis Ultra spectrometer using monochromatic Al Kα X-rays (1486.6 eV). Spectra were acquired from the ID surface of each sample using an X-ray analysis spot size of 700 μm×300 μm. Survey spectra were recorded with pass energy of 160 eV, from which the surface elemental compositions were determined. Selected high resolution spectra were recorded with pass energy of 20 eV, from which the chemical states of those elements were determined. Charge compensation was achieved using a beam of magnetically focused electrons as a flood current.

The standard photoelectron take-off angle used for analysis was 90° giving a maximum analysis depth in the range 5-8 nm.

In the ToFSIMS Analysis, ToFSIMS measurements were carried out on similarly prepared good, specimens using an ION-TOF ToF.SIMS 5 instrument equipped with a bismuth primary ion source ($Bi^+$ selected) and a pulsed electron flood source for charge compensation.

ToFSIMS spectra were acquired under static conditions from two different areas on the ID surface of all three samples; first area=400 μm×400 μm, second area=200 μm×200 μm (for improved mass resolution).

Figure 9:
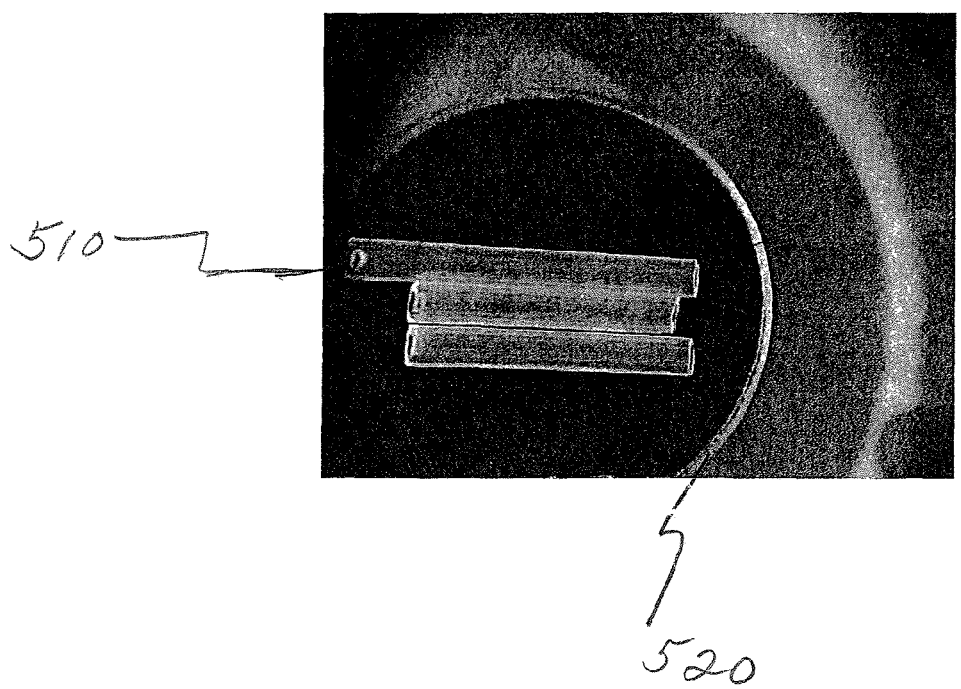
FIG. 9 shows the typical geometry for the samples presented to the x-ray beam in Example 1.

In the XRD Analysis, quantitative phase examination by X-ray Diffraction (XRD) was carried out using a Bruker New D8 Advanced instrument, as shown in FIG. 9. Good, poor and etched FEP tubing samples for the XRD analysis were prepared by cutting a 6 cm length from each sample and then cutting each length into three sections of ~2 cm length. These smaller segments 510 as shown in FIG. 9 were then tessellated back to back on to a cut silicon wafer 520 as shown in FIG. 9 so that the maximum amount of sample possible was present in the beam with minimum scatter from the sample holder. Thus, the accuracy of the amorphous content for the results was increased. FIG. 9 shows the typical geometry for the samples presented to the x-ray beam. The incident beam impinges from the top of the FIG. 9 and the detector is situated on the bottom of FIG. 9.

X-ray Diffraction data were collected from 5 to 50° two theta, with a step size of 0.2° and a dwell time per step of 0.5 seconds. The detector used was a LYNXEYE solid state position sensitive detector, where data were collected simultaneously over a three degree window for all 192 channels. The incident beam was conditioned using a Gobel mirror to provide a parallel beam geometry impinging on the sample. The parallel beam was passed through a 0.6 mm slit prior to irradiating the sample. Data were examined using diffract Eva software. The percentage crystallinity was evaluated from the total scattering area on the trade minus the coherent scattering from crystalline phases.

FIG. 10 lists the surface compositions in atomic percent (At. %) by XPS. For each of the three of the good, poor, and etched FEP tubing samples, the ID surface was dominated by fluorocarbon material which included primarily $CF_2$ groups but also some CF and $CF_3$ moieties. This fluorocarbon material was attributed to the FEP copolymer structure itself ($—[CF_2CF_2]_n—[CF_2CF(CF_3)]_m—$). The poor sample showed the highest level of fluorocarbon material. It was reasoned that the higher level of fluorocarbon material accounted for the higher hydrophobicity of the poor FEP tubing.

There was no evidence for perfluorooctanoic acid (PFOA, $CF_3[CF_2]_6COOH_1$, molecular mass=414) on any of the three samples. This molecule should have yielded the deprotonated molecular ion $CF_3[CF_2]_6COO^-$ at m/z $413^-$ in the negative ion ToFSIMS spectrum. No such signal was observed.

For all three of the good, poor and etched FEP sample tubings, a low level of hydrocarbon material was present including various oxygenated functionalities (ether/hydroxyl, carbonyl, carboxyl). Organo-nitrogen material was also present on the good and etched samples identified to ToFSIMS as amide and/or amine species. The overall level of hydrocarbon material was lowest on the poor sample, which correlated with the highest level of fluorocarbon.

For the poor FEP sample tubing only, a low level of silicon was detected and identified as poly-(dimethyl siloxane), $—[(CH_3)_2SiO]_n—$.

The detection of calcium and chlorine on the etched sample was attributed to a trace level of bleach residue such as calcium hypochlorate.

FIG. 11 shows the percentage crystallinity for each FEP sample tubing sample based on the XRD analysis.

There was a small but significantly higher level of crystallinity in the good tubing compared to the poor tubing (where both=TEFLON FEP TE-9302 N). The crystallinity observed for the etched tubing (FEP 100) fell between the other two samples.

What is claimed is:
1. An article comprising:
a section of tubing comprising a tubular body comprising a fluoropolymer, the tubular body including an interior surface defining a fluid passage through the tubular body, at least a first portion of the interior surface defining the fluid passage through the tubular body having a molar ratio of fluorine to oxygen of no greater than 30 to 1.
2. The article of claim 1, wherein the fluoropolymer is selected from the group consisting of a polytetrafluoroethylene, a fluorinated ethylene propylene, and a perfluoroalkoxy.

3. The article of claim 1, wherein the first portion has a first molar ratio of fluorine to oxygen of no greater than 30 to 1 and the remainder of the tubular body has a second molar ratio of fluorine to oxygen of greater than 30 to 1.

4. A product comprising:
the tubing of claim 1,
a fluid processing instrument operative to receive a fluid, the tubing attachable to the fluid processing instrument to deliver fluid to the instrument.

5. The product of claim 4, wherein the fluid processing instrument comprises an immunodiagnostic instrument.

6. An article comprising:
a section of tubing comprising a tubular body comprising a fluoropolymer, the tubular body including an interior surface defining a fluid passage through the tubular body, wherein at least a first portion of the interior surface defining the fluid passage through the tubular body has a second hydrophobicity less than that of a first hydrophobicity of a remainder of the tubular body.

7. The article of claim 6, wherein the fluoropolymer is selected from the group consisting of a polytetrafluoroethylene, a fluorinated ethylene propylene, and a perfluoroalkoxy.

8. A product comprising:
the tubing of claim 6,
a fluid processing instrument operative to receive a fluid, the tubing attachable to the fluid processing instrument to deliver fluid to the instrument.

9. The product of claim 8, wherein the fluid processing instrument comprises an immunodiagnostic instrument.

10. A process for altering an interior surface composition of a fluoropolymer tubing, comprising:
providing a section of tubing comprising a tubular body comprising a fluoropolymer, the tubular body including an interior surface defining a fluid passage through the tubular body, wherein the interior surface defining the fluid passage through the tubular body has a first hydrophobicity; and
exposing at least a first portion of the interior surface defining the fluid passage through the tubular body to an etching agent specific to fluoropolymers after which the first portion of the interior surface defining the fluid passage through the tubular body has a second hydrophobicity which is less than the first hydrophobicity.

11. The process of claim 10, the exposing step further comprising:
decreasing a first molar ratio of fluorine to oxygen of the first portion of the interior surface to no greater than 30 to 1.

12. The process of claim 10, wherein the etching agent comprises an active ingredient comprising sodium naphthalide.

13. The method of claim 10, further comprising:
providing a fluid processing instrument operative to receive a fluid for analysis;
attaching the tubular body to the fluid processing instrument; and
conveying the fluid for analysis through the fluid passage of the tubular body to the fluid processing instrument.

14. The process of claim 10, prior to the exposing step, further comprising:
heating the etching agent within a separate vessel to a temperature of between 50° C. and 60° C.

15. The process of claim 14, the heating step further comprising:
agitating the etching agent within the separate vessel.

16. The process of claim 10, after the exposing step, further comprising:
withdrawing the etching agent from the tubular body.

17. The process of claim 16, after the withdrawing step, further comprising:
flushing the interior surface of the tubular body at least a first time with an alcohol; and
rinsing the interior surface of the tubular body at least a first time with deionized water; and
drying the interior surface of the tubular body.

18. The process of claim 17, after the drying step, further comprising:
annealing the tubular body.

19. The process of claim 18, after the annealing step, further comprising:
cooling the tubular body to room temperature.

20. The process of claim 19, after the cooling step,
flushing the interior surface of the tubular body at least a first time with a bleach solution;
rinsing the interior surface of the tubular body at least a first time with water; and
drying the interior surface of the tubular body.

* * * * *